United States Patent [19]

Honma et al.

[11] Patent Number: 4,785,287

[45] Date of Patent: Nov. 15, 1988

[54] OIL CONDITION DETECTING APPARATUS

[75] Inventors: Masahiro Honma, Tokyo; Tadashi Nagai, Kanagawa, both of Japan

[73] Assignee: Nihon Radiator Co., Ltd., Tokyo, Japan

[21] Appl. No.: 135,020

[22] Filed: Dec. 18, 1987

[30] Foreign Application Priority Data

Dec. 25, 1986 [JP] Japan .................................. 61-314761

[51] Int. Cl.⁴ .............................................. G08B 21/00
[52] U.S. Cl. ......................................... 340/631; 73/64
[58] Field of Search ........................ 340/631, 603, 59; 73/64, 597, 599, 61 R

[56] References Cited

U.S. PATENT DOCUMENTS

| | | | |
|---|---|---|---|
| 3,876,935 | 4/1975 | Guillermie et al. ............ | 340/631 X |
| 4,008,464 | 2/1977 | Hobbie ............................. | 340/631 |
| 4,345,202 | 8/1982 | Nagy et al. ...................... | 73/64 X |
| 4,646,070 | 2/1987 | Yasuhara et al. ............... | 340/631 X |

Primary Examiner—Stewart J. Levy
Assistant Examiner—Joseph W. Roskos
Attorney, Agent, or Firm—Fitch, Even, Tabin & Flannery

[57] ABSTRACT

An instrument for detecting the condition of an oil is provided in which an ultrasonic wave having a predetermined waveform is propagated through the oil and assumes a change in waveform in accordance with the particular condition of the oil. The instrument includes an arrangement in which any change in the waveform of the propagated ultrasonic wave is translated into a change in terms of time involving the waveform, which is used for the detection of the particular condition of the oil.

14 Claims, 7 Drawing Sheets

OIL CONDITION DETECTING APPARATUS

FIELD OF INVENTION

The present invention relates to an oil condition detecting apparatus which detects the state or deterioration in the qualty of various kinds of oil including lubricating oils such as engine oil, hydraulic operating fluids and quenching oils.

BACKGROUND ART

A conventional oil condition detecing apparatus is known which is of the type described in, for example, Japanese patent application Public-Disclosure No. 61-20851. This conventional apparatus is arranged to detect any potential difference occurring between a reference electrode and a metal electrode, both of which are in contact with a lubricating oil, and to determine the extent of deterioration of the lubricating oil by comparing the potential difference with a refenence value. Further, this apparatus includes a temperature sensor for detecting the temperature of the lubricating oil for the purpose of providing for temperature compensation.

In this prior art, however, since detection of variations (or deterioration) in the oil condition is performed in such a manner that any variation of the electrostatic capacitance between the electrodes caused by the deterioration of the oil is obtained as a change in voltage and this change in voltage is directly measured, there are certain problems, as described below.

Firstly, the change in voltage that occurs between the electrodes which depends on the variation of the capacitance caused by the deterioration of the oil is very small. In particular, when the size of the electrodes is made relatively small in order to allow this apparatus to be adapted for use with engines for vehicles, the voltage change would become even smaller (the difference between the capacitances in the normal oil condition and in the deteriorated oil condition is usually in the range of 1-2 pF, the voltage change being proportional to this). Since detection of such a very small change suffers due to the poor S/N ratio, such very small changes in voltage would beoome undetectable under the influence of the inductance and stray capacitance that is involved with the leads extending from a sensor to a processing circuit if the length of the leads is substantial. It has therefore been difficult to put this conventional type of apparatus into practical use.

Additionally, accurate detection of such very small changes in voltage by the use of a conventional apparatus would require very large electrodes and this would in turn lead to the necessity for a large apparatus. Therefore, the conventional apparatus has very limited adaptability in general-purpose applications.

An object of the present invention, therefore, is to solve the problems mentioned above and to provide an oil condition detecting apparatus which can achieve accurate detection of the state of an oil with relatively compact apparatus.

Another object of the present invention is to provide such an oil condition detecting apparatus which is capable of achieving accurate detection of the extent of deterioration of an oil.

SUMMARY OF INVENTION

To achieve the above objects, the present invention provides an oil condition detecting apparatus which comprises ultrasonic wave transmitter and receiver means adapted to be immersed in an oil for transmitting an ultrasonic wave in response to a transmission timing signal, and for generating an ultrasonic reception signal in response to an ultrasonic wave received thereby; a reflector plate adapted to be immersed in said oil and disposed opposite to said ultrasonic wave transmitter and receiver means, for reflecting the transmitted ultrasonic wave from said ultrasonic wave transmitter and receiver means toward said ultrasonic wave transmitter and receiver means; oil condition detector means connected to receive the ultrasonic reception signal being generated from said ultrasonic wave transmitter and receiver means in response to the reflected ultrasonic wave, said oil condition detector means being operative to sense a change in the waveform of the ultrasonic reception signal in terms of a change in time, based on the fact that the waveform of the ultrasonic reception signal varies in accordance with variations in the condition of said oil, and to generate an oil condition signal representative of the condition of said oil on the basis of the change in time; and indicator means connected to receive said oil condition signal and indicate the state of said oil on the basis of said oil condition signal.

According to an embodiment of the present invention, said oil condition detector means is operative to detect changes in the waveform of ultrasonic reception signals as changes in the delay that proceeds from the time of generation of a transmission timing signal to the time at which an ultrasonic reception signal exceeds a predetermined level. In this way the oil condition detector means generates an oil condition signal based on the detection of changes in this delay.

According to another embodiment of the present invention, said oil condition detector means is operative to detect changes in the waveform of an ultrasonic reception signal as changes in the duration of a period during which the ultrasonic reception signal exceeds a predetermined level. In this case the detector means generates an oil condition signal based on the detection of changes in that duration.

The present invention will be more fully described hereinafter with reference to embodiments thereof and the associated drawings.

DETAILED DESCRIPTION OF INVENTION

Figure 1:
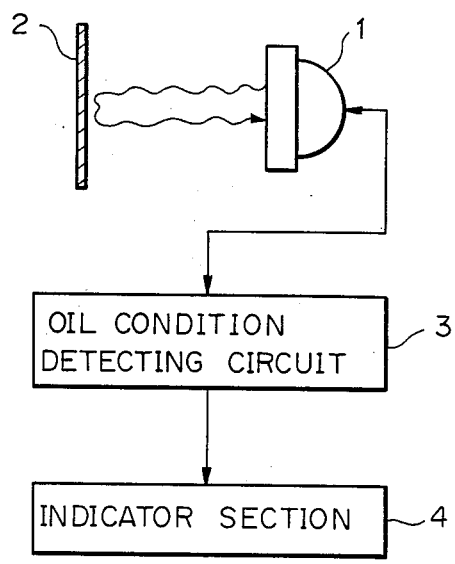
FIG. 1 is a schematic diagram ilustrating an oil condition detecting instrument according to the present invention.

First of all, an oil condition detecting instrument according to the present invention will be generally described with reference to the schematic diagram in FIG. 1. The oil condition detecting instrument comprises an ultrasonic wave transmitter/receiver device 1 adapted to be immersed in an oil and to transmit an ultrasonic wave and receive the same ultrasonic wave after it has been propagated through the oil; a reflector plate 2 disposed opposite the ultrasonic wave transmitter/receiver device 1; an oil condition detecting circuit 3, the function of which is based on the fact that a waveform of the received ultrasonic wave changes in response to any change in the oil condition, the circuit being designed to sense any variation of the waveform as a variation of time and to produce an oil condition signal in correspondence with the change in time; and an indicator section 4 indicating the oil condition in response to the oil condition signal.

The oil condition detecting instrument of the present invention which has the general construction described above operates as follows. An ultrasonic wave generated by the ultrasonic transmitter/receiver device 1 is propagated through the oil, reflected by the reflector plate 2, and then received by the transmitter/receiver device 1. There is a change in the waveform of the received ultrasonic wave which occurs due to deterioration of the oil. Then, the oil condition detector circuit 3 senses the change in the waveform of the received ultrasonic wave as a ohange in time, which is either a change in the time required to receive a sound wave of a predetermined amplitude level (that is, a change in the length of time from the transmission of an ultrasonic wave to the reception of that ultrasonic wave which is of the predetermined amplitude level), or alternatively a change in the time width of an ultrasonic wave having an amplitude above the predetermined amplitude level (that is, a change in the length of time from the moment when reception of the wave that is above the predetermined amplitude leve begins to the moment when the reception of that wave ends). Then the circuit 3 produces an oil condition signal representative of oil within an oil pan (not shown) of the automobile engine the condition of the oil in correspondence with the change in time. The oil condition signal is applied to the indicator section 4 where the oil condition is indicated.

Therefore, in accordance with the oil condition detecting instrument of the present invention, since a change in the oil condition is detected as a change in the waveform of an ultrasonic wave which is in turn sensed in terms of a change in time, the S/N ratio is improved and accurate detection of the oil condition can be achieved with an instrument that is small in size.

Referring now to the drawings, an embodiment of the present invention will be described in detail in connnection with, for instance, an oil deterioration detecting instrument that may be provided for an automobile engine for the purpose of detecting the condition of an oil, particularly deterioration of the oil.

Figure 2:
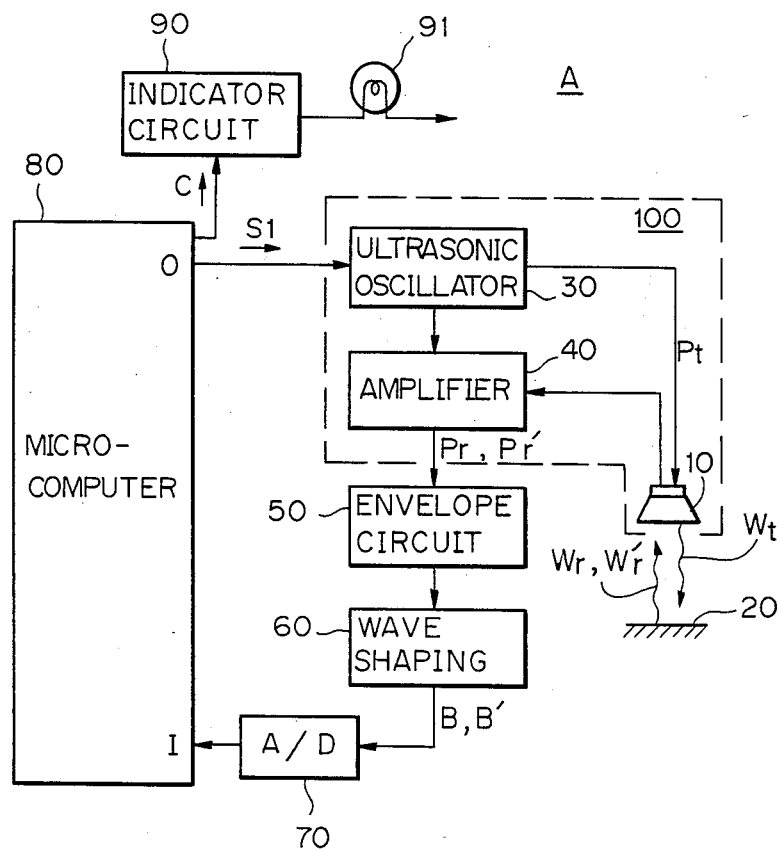
FIG. 2 is a block diagram showing an oil condition detecting instrument which is an embodiment of the present invention.

With reference to FIG. 2, the oil deterioration detecting instrument A which represents an embodiment of the present invention comprises an ultrasonic wave transmitter/receiver element 10, a reflector plate 20, an ultrasonic oscillator circuit 30, an amplifier circuit 40, an envelope circuit 50, a wave shaping circuit 60, an A/D converter 70 and a microcomputer 80.

The ultrasonic wave trasmitter/receiver element 10 forms, together with the ultrasonic oscillator circuit 30 and the amplifier circuit 40, an ultrasonic wave transmitter/receiver 100. The element 10 is immersed in oil within an oil pan (not shown) of the automobile engine and is disposed opposite the reflector plate 20, which is also immersed in the oil pan, so that the transmitted ultrasonic wave reflected from the reflector plate 20 may be received by the element 10.

The ultrasonic oscillator oirouit 30 is a circuit which upon receiving from the microcomputer 80 a transmission timing signal S1 having a predetermined width (t2−t1), shown in FIG. 3(a), produces an ultrasonic signal Pt having the same duration as the width of the signal S1, as shown in FIG. 3(b). This ultrasonic signal Pt causes the element 10 to transmit a corresponding ultrasonic wave Wt having a substantially constant amplitude.

The amplifier circuit 40, which forms a part of the ultrasonic wave transmitter/receiver 100, operates to amplify an ultrasonic signal, which is generated from the ultrasonic wave transmitter/receiver element 10 in response to a reflected ultrasonic wave Wr (or Wr') incident upon the element 10, so that the amplifier 40 produces a reflected ultrasonic signal Pr (or Pr') as shown in FIG. 3(c) [or FIG. 3(d)]. This amplifier circuit 40 is connected to receive a signal from the ultrasonic oscillation circuit 30 so that the circuit 40 is disabled during the transmission of the ultrasonic wave Wt. The reflected ultrasonic signals Pr and Pr' represent the ultrasonic waves which result when the transmitted ultrasonic wave Wt is reflected by the reflector plate 20 and is also attenuated during propagation through the oil; Pr represents the reflected ultrasonic wave when the oil is in a fresh condition and Pr' represents the reflected ultrasonic wave when the condition of the oil has deteriorated.

As seen in FIGS. 3(c) and (d), the attenuation of the reflected ultrasonic signal Pr' is greater than that of the signal Pr. This increased attenuation occurs from an increased deterioration of the oil, that is an increase in the amount of solid particles, such as metal dust and carbon particles, which are contained in the oil.

The envelope circuit 50 is the envelope detector circuit which operates to shape the reflected ultrasonic signal Pr (or Pr') into a signal having the waveform of an envelope which results from the amplitude peak points of the signal Pr being connected together, as shown in FIG. 3(e). The wave shaping circuit 60 generates from the envelope signal output of the envelope circuit 50 a shaped signal B (or B') shown in FIG. 3(f), the level of which is high during the time period when the amplitude of the envelope signal exceeds a predetermined threshold level S. The A/D converter 70 operates to convert the shaped signal generated from the shaping circuit 60 into a digital signal and then output it to the microcomputer 80.

The microcomputer 80 forms, together with the envelope circuit 50, the wave shaping circuit 60, and the A/D converter 70, the oil condition detector circuit. This microcomputer 80 is arranged to output the transmission timing signal S1 at a predetermined cycle. Also, the microcomputer 80, in accordance with the flow shown in the flow chart of FIG. 4, detects the extent of deterioration of the oil on the basis of the information carried by the shaped signal B or B' which is supplied by the A/D converter 70, so that the microcomputer 80 outputs a deterioration signal C when it is detected that the oil has deteriorated to a predetermined extent.

More specifically, the microcomputer 80 obtains a delay time Td (=t3−t1) [or Td' (=t3'−t1)] which is measured from the time t1 at which the transmission timing signal S1 was output to the time t3 (or t3') at which the shaped signal B (or B') is input to the microcomputer 80. This delay time Td is compared with a reference value Tn whch is a criterion for measuring the predetermined extent of deterioration referred to above. When the delay time Td is larger than the reference value Tn (Td>Tn), the deterioration signal C is output as an oil condition signal.

An indicator circuit 90 is a circuit which operates in response to the deterioration signal C to illuminate a warning lamp 91 which in turn serves to call the user's attention to the need to change the oil which has deteriorated in quality with fresh oil.

The operation of the above described embodiment will now be described.

When the ultrasonic oscillator circuit 30 receives the transmission timing signal S1 shown in FIG. 3(a) from the microcomputer 80, the ultrasonic oscillator circuit 30 will perform oscillation to generate the transmitting ultrasonic signal Pt shown in FIG. 3(b) which causes the ultrasonic wave transmitter/receiver element 10 to generate the ultrasonic wave Wt.

The transmitted ultrasonic wave Wt is propagated through the oil, reflected by the reflector plate 20, and then received by the element 10. The reflected ultrasonic wave Wr is attenuated during propagation through the oil before being received by the element 10, and the degree of attenuation of the received ultrasonic wave Wr depends on the extent of deterioration of the oil, as seen from the signals Pr and Pr' shown in FIGS. 3(c) and (d). That is, the more the oil is deteriorated by the accumulation of solid particles such as metal dust and carbon particles contained in the oil, the higher the degree of attenuation of the reflected ultrasonic wave becomes, as seen from the reflected ultrasonic signal Pr'.

The reflected ultrasonic signal Pr or Pr' received by the ultrasonic transmitter/receiver element 10 in that manner then undergoes a waveform processing by the envelope circuit 50 in which the waveform of the reflected ultrasonic signal is shaped into the envelope waveform thereof. Then, the envelope waveform is shaped by the wave shaping circuit 60 which derives the portion of the envelope waveform beyond the predetermined level S to shape it into that of the shaped signal B (or B') shown in FIG. 3(f).

With the shaped signal B (or B'), the degree of attenuation of the reflected ultrasonic signal Pr (or Pr') is detected either as the delay time Td (or Td') beginning at the time of the oscillation and ending at the time of the reception of the shaped signal B (or B'), or as the time period of the duration of the shaped signal B (or B'). Thus, the degree of attenuation can be obtained in terms of the dimension of time.

Figure 3:
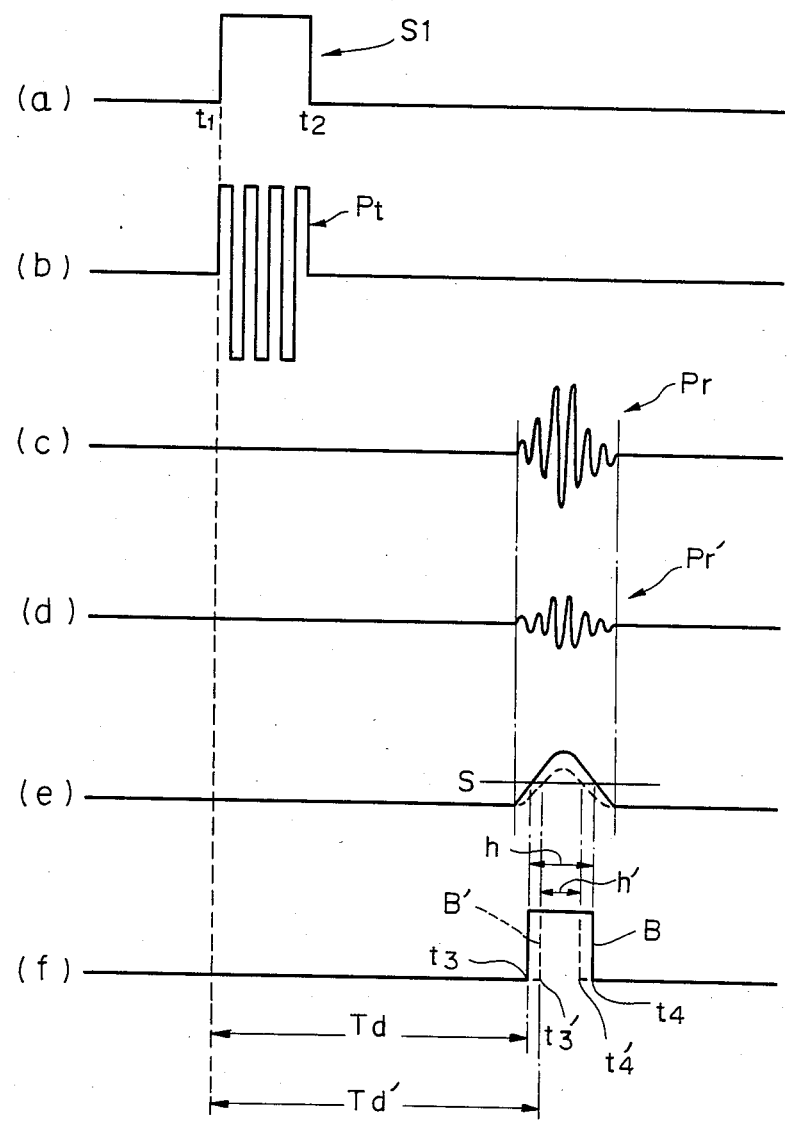
FIG. 3 is a waveform diagram illustrating various signals appearing in the instrument shown in FIG. 2.

As shown in FIG. 3, when the extent of deterioration of the oil is relatively small, the degree of attenuation of the reflected ultrasonic signal Pr is low. Then, since the rising of the envelope signal [shown in a solid line in FIG. 3(e)] for the signal Pr is fast and thus the time required for the envelope signal to reach the threshold level S is short, the delay time Td is short while the width or duration h of the shaped signal B [shown in a solid line in FIG. 3(f)] derived from the envelope signal is long.

On the other hand, when the extent of deterioration of the oil is greater, the degree of attenuation of the reflected ultrasonic signal Pr' is high. In this case, since the rising of the envelope signal [shown by a dotted line in FIG. 3(e)] for the signal Pr' is slow and the time required for the envelope signal to reach the threshold level S is long, the delay time Td' is long while the duration h' of the shaped signal B' [shown in a dotted line in FIG. 3(f)] for the envelope signal is short.

Figure 4:
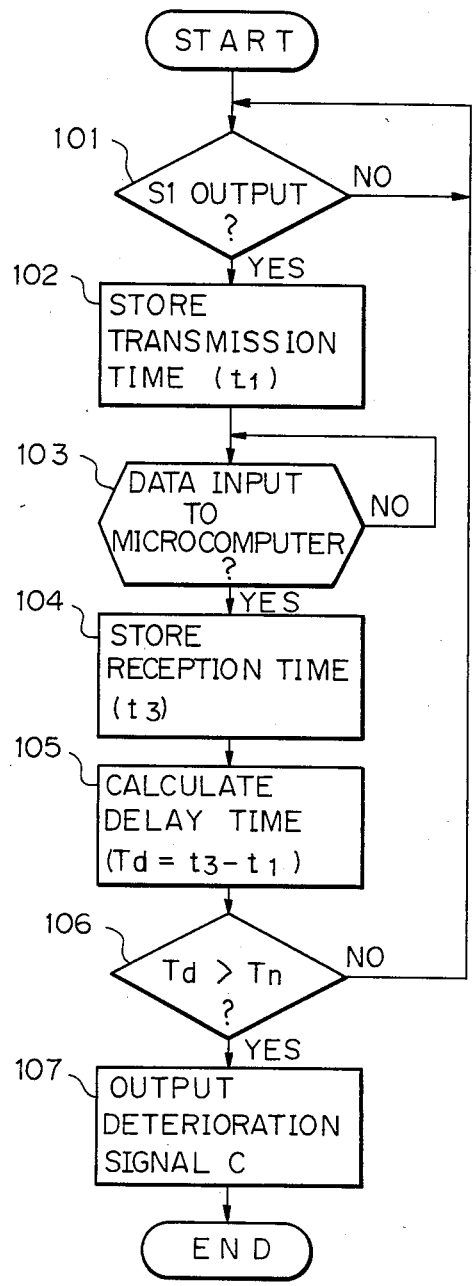
FIG. 4 is a flow chart illustrating a flow of processings performed by the microcomputer of the instrument represented by the embodiment shown in FIG. 2 used in detection of the deterioration of an oil on the basis of a delay time.

Next, the operation of the microcomputer 80 will be described with reference to the flow chart of FIG. 4.

Firstly, in step 101, it is determined whether the transmission timing signal S1 has been output or not. If the result of this decision is YES, the flow proceeds to step 102 in which the transmission time t1 is stored. Then, the flow proceeds to step 103 where it is determined whether data, that is, the shaped signal B, has been input to the input port of the microcomputer or not. If the result of the decision is YES, the flow proceeds to step 104 in which the input time t3 of the shaped signal B is read and stored in a predetermined register.

Then, in step 105, the transmission time t1 of the transmission timing signal S1 is substracted from the input time t3 stored in the register to obtain the delay time Td. Then, in step 106, the delay time Td is compared with the reference value Tn to see if Td is greater than Tn. If NO, the flow returns to step 101 for the next transmission of an ultrasonic wave. If YES in step 106, indicating that the delay time Td exceeds the reference value Tn, it proceeds to step 107 in which a deterioration signal C indicating that the oil has deteriorated is output. Then, the indicator circuit 90 which receives the deterioration signal C illuminates the warning lamp 91 to call the user's attention to the need to change the oil.

As explained above, according to the oil deterioration detecting instrument A of the embodiment of the present invention, the following advantages are obtained.

Firstly, since the oil condition detector circuit, which is operative to sense the state of deterioration of an oil as a change in the waveform of an ultrasonic wave and to sense this waveform change in terms of a change in time, and is arranged to comprise the envelope circuit 50, the wave shaping circuit 60, the A/D converter 70, and the microcomputer 80, not only is the S/N ratio improved, but also accurate detection of the state of deterioration of an oil can be achieved even with a comparatively small instrument.

Secondly, since a change in a waveform can generally be sensed in terms of a change in time much easier and much more accurately than in terms of a difference in level or a value of an integration, the present detecting instrument is capable of providing accurate detection of an oil condition in a facilitated manner as compared with other instruments of the type in which an oil condition is sensed as a change in the waveform of an ultrasonic wave.

Thirdly, since the present detecting instrument employs a ultrasonic wave transmitter/receiver element 10 which serves both for the transmission and reception of the ultrasonic wave, the entire instrument can be made oompact.

While the embodiment has been described and illustrated as being applied to an automobile engine. the present invention is not limited in its application to this usage and may be applied to other usages involving such oils as lubricating oil, quenching oil and hydraulic operating oil.

Further, while the above described embodiment has been described as one in which the deterioration of an oil is detected on the basis of the delay time of a shaped signal, the present invention may be modified to detect the deterioration of an oil on the basis of the width or duration (h) of a shaped signal. In such cases, the processings performed by the microcomputer 80 will be as shown in the flow chart of FIG. 5. In this flow chart, steps 111, 113 and 117 are the same as the steps 101, 103 and 107 of FIG. 4, respectively. In step 113, if the input of data is detected, the flow then proceeds to step 114 where the beginning and ending times of the data input are stored in the form of the shaped signal B. Then, in step 115, a duration h is calculated, and in step 116 a check is made to determine whether or not the condition h<hn has been fulfilled. If YES, a deterioration signal C is output in step 117, as illustrated in FIG. 4.

Figure 5:
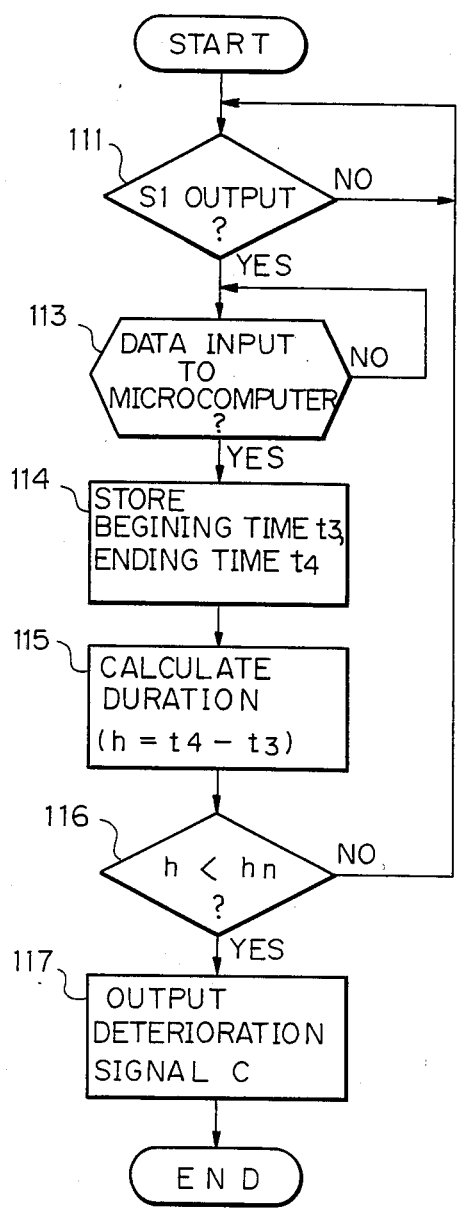
FIG. 5 is a flow chart illustrating an alteration of the flow of processings shown in FIG. 4 used in detection of the deterioration of an oil on the basis of the duration of a shaped signal.
Figure 6:
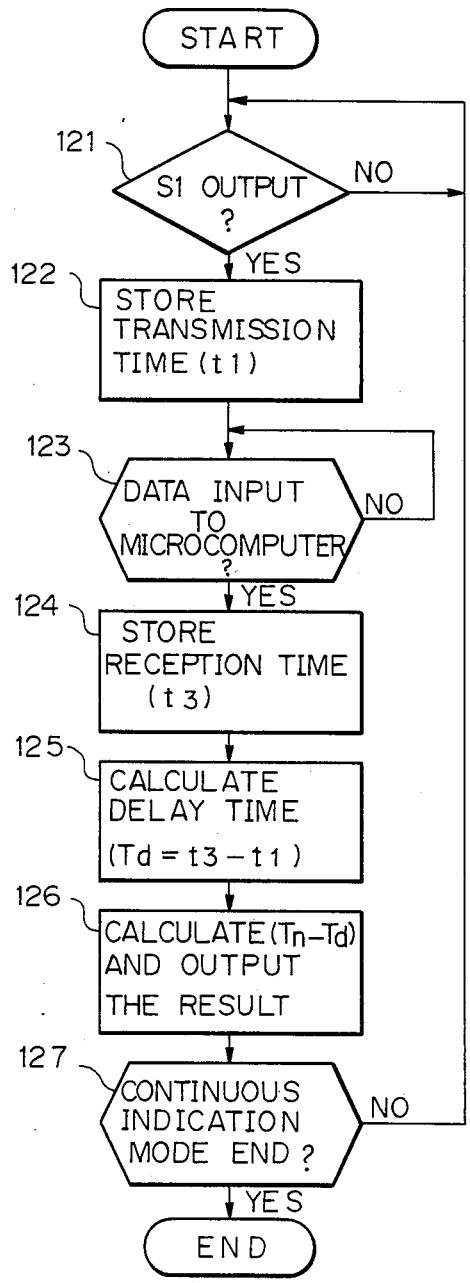
FIG. 6 is a flow chart of a modification of the flow of processings shown in FIG. 4, illustrating a continuous indication flow for providing a continuous indication of the deterioration of an oil.

Furthermore, while the above embodiment has been described as one wherein the deterioration of an oil is indicated by illuminating a warning lamp, the present invention may be modified to provide a continuous indication of the condition of deterioration of the oil. In this instance, a continuous indication flow is executed by the microcomputer 80 as shown in FIG. 6. In this continuous indication flow, steps 121–125 are the same as the steps 101–105 of FIG. 4, respectively. After the delay time Td has been calculated in step 125, the difference (Tn−Td) between the reference value Tn and the delay time Td is calculated and the result is output to the indicator circuit 90. This indicator circuit 90 which receives the result generates an appropriately scaled signal representing this result, which is in turn applied to an indicator (not shown) suitable for continuous indication. Next, in step 127, a check is made to determine whether or not a command has been given for the termination of the mode of continuous indication, and if NO, the flow loops to step 121. If YES, indicating the presence of such a command the flow ends. It should be noted that this feature of continuous indication can be similarly applied to the previous method illustrated in FIG. 5 in which the duration h is calculated to determine the extent of deterioration. In such a case, step 116 in the flow chart of FIG. 5 is replaced with a step in which a difference (h−hn) between the calculated duration h and the reference value hn is calculated and the result output, and also step 117 in the same flow chart is replaced with step 127.

Figure 7:
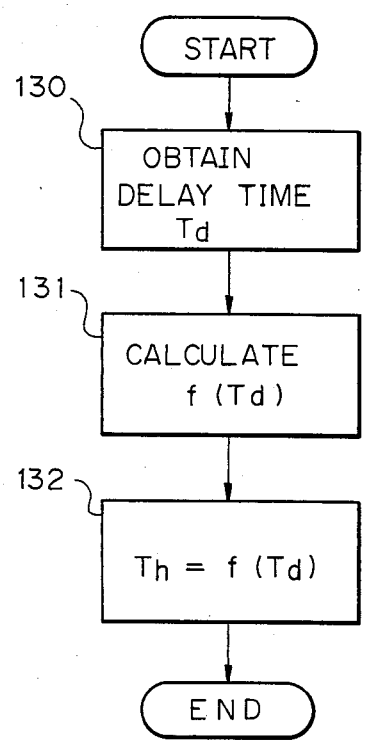
FIG. 7 is a flow chart of an updating flow which updates a reference value used as a criterion for measuring the deterioration of an oil.

Furthermore, while the above embodiment has been described as being arranged to compare the delay time with a predetermined reference value, the present invention may be modified in such a manner that the predetermined reference value is updated on the basis of a delay time which is obtained from fresh oil immediately after an oil change. In this connection, an updating flow executed by the microcomputer 80 is shown in FIG. 7. This updating flow is entered in response to a reset button (not shown) which is depressed after the oil change. At first, in step 130, a delay time Td is obtained through the same processings as in the steps 101–105 of FIG. 4. Then, f(Td) is obtained in step 131 by calculating the equation $f(Td)=Td+\alpha$ [or equation $f(Td)=\beta \cdot Td$] (where $\alpha$ and $\beta$ are constants). Then, in step 132, the reference value Tn is made equal to the calculated f(Td). It should be noted that this updating flow can be applied to the method of FIG. 5 in which the duration h is calculated. In this case, alterations are made so that a duration h is obtained in step 130, that f(h) is obtained in step 131 by calculating the equation $f(h)=h-\gamma$ [or equation $f(h)=\theta \cdot h$] (where $\gamma$ and $\theta$ are constants), and that the reference value hn is made equal to f(h) in step 132.

As described hereinabove, since the oil condition detecting apparatus according to the present invention is constructed as a means that incorporates an oil condition detector circuit which detects any change in an oil condition as a change in the waveform of an ultrasonic wave and senses the change in the waveform as a change in time, the invention provides the advantages that the S/N ratio is improved and the oil condition may be accurately detected even with an apparatus that is small in size.

Further, since the apparatus according to the present invention employs an ultrasonic wave transmitter/receiver which can both transmit and receive ultrasonic waves, the invention provides the advantage that the apparatus can be made compact in size.

Additionally, since a change in the waveform can usually be sensed as a change in time much easier and much more accurately than as a difference in level or as an integrated value, the present invention provides the advantage that it is capable of providing for accurate detection of an oil condition in a facilitated manner as compared with other instruments of the type in which an oil condition is detected as a change in the waveform of an ultrasonic wave.

What is claimed is:

1. An oil condition detecting apparatus for detecting the condition of an oil comprising:
   a. ultrasonic wave transmitter and receiver means adapted to be immersed in an oil for transmitting an ultrasonic wave in response to a transmission timing signal, and for responding to an ultrasonic wave received thereby to generate an ultrasonic reception signal;
   b. a reflector plate adapted to be immersed in said oil and disposed opposite said ultrasonic wave transmitter and receiver means, for reflecting the transmitted ultrasonic wave from said ultrasonic wave transmitter and receiver means toward said ultrasonic wave transmitter and receiver means;
   c. oil condition detector means connected to receive the ultrasonic reception signal generated by said ultrasonic wave transmitter and receiver means in response to the reflected ultrasonic wave, said oil condition detector means being operative to sense a change in the waveform of the ultrasonic reception signal in terms of a change in time, based on the fact that the waveform of the ultrasonic reception signal varies in dependence upon a change in the condition of said oil, and to generate an oil condition signal representative of the condition of said oil in correspondence with the change in time; and
   d. indicator means connected to receive said oil condition signal for indicating the condition of said oil on the basis of said oil condition signal.

2. An apparatus as set forth in claim 1, wherein said oil condition detector means is operative to detect the change in the waveform of the ultrasonic reception signal as a change in the length of a delay represented by the time from the generation of the transmission timing signal to the time at which the ultrasonic reception signal exceeds a predetermined level, whereby said oil condition detector means generates said oil condition signal based on the change in the delay time detected.

3. An apparatus as set forth in claim 2, wherein said oil condition detector means includes:
envelope detecting means for receiving said ultrasonic reception signal to generate an envelope signal representative of the envelope of said ultrasonic reception signal;
shaping means for comparing said envelope signal with a predetermined threshold level to generate a shaped signal during the time period when the envelope signal exceeds the predetermined threshold level; and
delay time detecting means for detecting the length of the delay from the time of the generation of said transmission timing signal to the beginning of said shaped signal.

4. An apparatus as set forth in claim 3, wherein said oil condition detector means further includes a first deterioration detecting means, said first deterioration detecting means including:
a first reference time generating means for generating a first predetermined reference time representative of said delay at a predetermined level of deterioration of said oil; and
a first comparing means for comparing said detected delay from said delay time detecting means with said first predetermined reference time from said first reference time generating means to generate said oil condition signal representing a predetermined extent of deterioration of said oil when said detected delay exceeds the first predetermined reference time.

5. An apparatus as set forth in claim 4, wherein said oil condition detector means further includes:
a first updating means for updating said first predetermined reference time on the basis of said detected delay generated by said delay time detecting means at the time when said oil is fresh.

6. An apparatus as set forth in claim 3, wherein said oil condition detector means further includes:
a first converting means for converting said detected delay from said delay time detecting means to a value representing the extent of deterioration of said oil so as to generate said oil condition signal representing said extent of deterioration.

7. An apparatus as set forth in claim 2, wherein said oil condition detector means is operative to detect the change in the waveform of the ultrasonic reception signal as a change in the duration of a period during which said ultrasonic reception signal exceeds a predetermined level, whereby said oil condition detector means generates said oil condition signal based on the change in the duration detected.

8. An apparatus as set forth in claim 7, wherein said oil condition detector means includes:
envelope detecting means for receiving said ultrasonic reception signal to generate an envelope signal representative of the envelope of said ultrasonic reception signal;
shaping means for comparing said envelope signal with a predetermined threshold level to generate a shaped signal during the period when the envelope signal exceeds the predetermined threshold level; and
duration detecting means for detecting the duration of said shaped signal.

9. An apparatus as set forth in claim 8, wherein said oil condition detector means further includes a second deterioration detecting means, said second deterioration detecting means including:
a second reference time generating means for generating a second predetermined reference time representative of said duration at a predetermined level of deterioration of said oil; and
a second comparing means for comparing said detected duration from said duration detecting means with said second predetermined reference time from said second reference time generating means to generate said oil condition signal representing a predetermined extent of deterioration of said oil when said detected duration is less than the second predetermined reference time.

10. An apparatus as set forth in claim 9, wherein said oil condition detector means further includes:
a second updating means for updating said second predetermined reference time on the basis of said detected duration generated by said duration detecting means at the time when said oil is fresh.

11. An apparatus as set forth in claim 8, wherein said oil condition detector means further includes:
a second converting means for converting said detected duration from said duration detecting means to a value representative of the extent of deterioration of said oil so as to generate said oil condition signal representing said extent of deterioration.

12. An apparatus as set forth in claim 1, wherein said oil is oil in the oil pan of an engine.

13. An oil condition detector apparatus for detecting the condition of an oil comprising:
a. ultrasonic wave transmitter and receiver means adapted to be immersed in an oil for transmitting an ultrasonic wave in response to a transmission timing signal, and for responding to an ultrasonic wave received thereby to generate an ultrasonic reception signal;
b. a reflector plate adapted to be immersed in said oil and disposed opposite said ultrasonic wave transmitter and receiver means, for reflecting the transmitted ultrasonic wave from said ultrasonic wave transmitter and receiver means toward said ultrasonic wave transmitter and receiver means;
c. oil condition detector means connected to receive the ultrasonic reception signal generated by said ultrasonic wave transmitter and receiver means in response to the reflected ultrasonic wave, said oil condition detector means being operative to detect a change in the waveform of the ultrasonic reception signal as a change in the length of a delay from the time of generation of the transmission timing signal to a time at which the ultrasonic reception signal exceeds a predetermined level, and to generate an oil condition signal representative of the condition of said oil based on the change in the length of the delay detected; and
d. indicator means connected to receive said oil condition signal for indicating the condition of said oil on the basis of said oil condition signal.

14. An oil condition detector apparatus for detecting the condition of an oil comprising:
a. ultrasonic wave transmitter and receiver means adapted to be immersed in an oil for transmitting an ultrasonic wave in response to a transmission timing signal, and for responding to an ultrasonic wave received thereby to generate an ultrasonic reception signal;

b. a reflector plate adapted to be immersed in said oil and disposed opposite said ultrasonic wave transmitter and receiver means, for reflecting the transmitted ultrasonic wave from said ultrasonic wave transmitter and receiver means toward said ultrasonic wave transmitter and receiver means;

c. oil condition detector means connected to receive the ultrasonic reception signal generated by said ultrasonic wave transmitter and receiver means in response to the reflected ultrasonic wave, said oil condition detector means being operative to detect a change in the waveform of the ultrasonic reception signal as a change in the duration of a period during which said ultrasonic reception signal exceeds a predetermined level, and to generate an oil condition signal representative of the condition of said oil based on the change in the duration detected; and d. indicator means connected to receive said oil condition signal for indicating the condition of said oil on the basis of said oil condition signal.

* * * * *

UNITED STATES PATENT AND TRADEMARK OFFICE
CERTIFICATE OF CORRECTION

PATENT NO. : 4,785,287

DATED : November 15, 1988

INVENTOR(S) : Masahiro HONMA et al.

It is certified that error appears in the above-identified patent and that said Letters Patent is hereby corrected as shown below:

<u>FACE OF PATENT</u>

Under "References Cited", insert --Foreign Documents, Japanese Patent 61 20851--.

<u>IN THE SPECIFICATION</u>:

Column 1, line 20, change "refenence" to --reference--.

Column 1, line 44, change "beoome" to --become--.

Column 2, line 48, change "ilustrating" to --illustrating--.

Column 3, line 34, change "ohange" to --change--.

Column 3, line 44, change "leve" to --level--.

Column 3, lines 46, 47, delete "oil within an oil pan (not shown) of the automobile engine".

Column 3, lines 59, 60, change "connnection" to --connection--.

Column 4, line 3, change "trasmitter" to --transmitter--.

Column 4, line 11, change "I0" to --10--.

Column 4, line 12, change "oirouit" to --circuit--.

UNITED STATES PATENT AND TRADEMARK OFFICE
CERTIFICATE OF CORRECTION

PATENT NO. : 4,785,287
DATED : November 15, 1988
INVENTOR(S) : Masahiro HONMA et al.

It is certified that error appears in the above-identified patent and that said Letters Patent is hereby corrected as shown below:

Column 5, line 10, change "whch" to --which--.

Column 6, line 65, change "oompact" to --compact--.

Column 6, line 67, change the period to a comma.

Column 7, line 58, change "exeouted" to --executed--.

IN THE CLAIMS:

Claim 8, Column 9, line 65, change "exoeeds" to --exceeds--.

Claim 13, Column 10, line 34, change "oomprising" to --comprising--.

Claim 14, Column 10, line 64, change "oomprising" to --comprising--.

Claim 14, Column 10, line 65, change "reoeiver" to --receiver--.

Signed and Sealed this

Sixth Day of June, 1989

*Attest:*

DONALD J. QUIGG

*Attesting Officer*  *Commissioner of Patents and Trademarks*